(12) United States Patent
Bedbury et al.

(10) Patent No.: US 7,084,206 B2
(45) Date of Patent: Aug. 1, 2006

(54) PROCESS FOR PREPARING PHENYLORGANOSILICON INTERMEDIATES

(75) Inventors: Curtis J. Bedbury, Midland, MI (US); John P. Cannady, Midland, MI (US); Binh T. Nguyen, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 591 days.

(21) Appl. No.: 10/117,259

(22) Filed: Apr. 4, 2002

(65) Prior Publication Data

US 2003/0191238 A1 Oct. 9, 2003

(51) Int. Cl.
*C08L 83/00* (2006.01)
(52) U.S. Cl. .................................................. 524/858
(58) Field of Classification Search ................ 524/858
See application file for complete search history.

(56) References Cited

U.S. PATENT DOCUMENTS

| 2,795,627 A | 6/1957 | Ramsden |
| 2,795,628 A | 6/1957 | Ramsden |
| 2,894,012 A * | 7/1959 | Rosenberg et al. ......... 556/480 |
| 5,596,120 A | 1/1997 | Bank et al. |

FOREIGN PATENT DOCUMENTS

| JP | 03-109389 | * | 9/1991 |
| RU | 2174124 | * | 9/2001 |

OTHER PUBLICATIONS

Coates et al., Organomethallic Compounds, vol. 1, pp. 76-103, 1967, Methuen and Co Ltd, London, U.K.*
Coates et al., Organomethallic Compounds, vol. 1, pp. 76-103, 1967, Methuen and Co Ltd, London, U.K; pp. 80-82.*
Coates, et al., Organometallic Compounds, vol. 1, pp. 76-103 (1967) Methuen and Co. Ltd, London, U.K.
Kirk/Othmer, Encylopeida of Chemical Technology, vol. 10, 721-734 (1966) The Interscience Encylopedia, Inc., NY N.Y.

* cited by examiner

*Primary Examiner*—Johann Richter
*Assistant Examiner*—Chukwuma Nwaonicha
(74) *Attorney, Agent, or Firm*—Robert L. McKellar; McKellar IP Law, PLLC

(57) ABSTRACT

A method for preparing phenyl-containing organosilicon intermediates using an aromatic halogenated solvent during the coupling reaction involving a phenyl Grignard reagent and a precursor silane. The process comprises contacting a phenyl halide with magnesium in a solvent such as ether, or an aromatic halogenated/ether solvent mixture to form a Grignard reagent, and contacting the Grignard reagent with a precursor chlorosilane in aromatic halogenated solvent to form the desired organosilicon intermediates, and then filtering and distilling to acquire the organosilicon intermediate reaction product.

19 Claims, No Drawings

PROCESS FOR PREPARING PHENYLORGANOSILICON INTERMEDIATES

The present invention relates to a method for preparing phenyl-containing organosilicon intermediates using an aromatic halogenated solvent during the coupling reaction involving a phenyl Grignard reagent and a precursor halosilane. The process comprises contacting a phenyl halide with magnesium in a solvent such as ether, or aromatic halogenated solvent/ether mixtures to form a Grignard reagent, and thereafter contacting the Grignard reagent with a precursor chlorosilane in aromatic halogenated solvent to form the desired organosilicon intermediates, and then filtering and distilling to acquire the organosilicon intermediate reaction product.

The inventors of the present invention have found that the use of aromatic halogenated solvents in conjunction with ethers, the traditional Grignard reaction solvents, results in lower reaction temperatures, the ability to separate the desired organosilicon intermediate from the by-produced magnesium halides with ease which results in higher yields of purer organosilicon intermediates, and, created the ability to reduce the amount of waste solvent that normally occurs with the traditional Grignard process.

BACKGROUND OF THE INVENTION

The reaction of organic halides with magnesium metal in the presence of oxygenated solvents such as dialkyl ethers to form reactive complexes typically referred to as Grignard reagents is well known. The production and reactions of Grignard reagents has been the subject of books and numerous review articles. Such reviews are provided, for example, in Coates, et al., ORGANOMETALLIC COMPOUNDS, Vol. 1, pp. 76–103, (1967), Methuen and Co. Ltd, London, U.K.; and in Kirk/Othmer, ENCYCLOPEDIA OF CHEMICAL TECHNOLOGY, Vol. 10, 721–734 (1966), The Interscience Encyclopedia, Inc., NY, N.Y. The structure of the Grignard reagent has not been determined with certainty, however it is generally believed that the Grignard reagent exists as a complex in solution and that solvent can play a critical role in such complex formation. The unpredictable effect of solvent on the formation and reactivity of Grignard reagents is discussed in the above cited review articles, and the inventors herein believe, but should not be held to such a theory, that the following reaction equations may be the actual mechanisms in the inventive process, wherein by way of example, phenyl chloride is used as the organic halide reactant:

It is also well known from the patent literature that phenyl magnesium chloride as a Grignard reagent can be prepared by reacting chlorobenzene with magnesium at reflux temperatures in the presence of a catalytic amount of a halide catalyst selected from the class consisting of carbon tetrachloride and silicon tetrachloride. Cf. U.S. Pat. No. 2,795,627 issued to Ramsden on Jun. 11, 1957. Also, Ramsden teaches, in U.S. Pat. No. 2,795,628, that also issued on Jun. 11, 1957, that phenylmagnesum chloride Grignard reagents can be prepared by reacting magnesium having an oxidized surface, with sulfur-free aromatic halogenated agents at reflux temperatures.

Finally, it is important to note that U.S. Pat. No. 5,596,120, that issued to Bank, et al, on Jan. 21, 1997 teaches the preparation of alkyl-containing organosilanes in a one-step process that comprises contacting magnesium metal with a mixture comprising an organic halide and a halosilane in a co-solvent comprising about one to 15 moles of a dialkyl ether and a mole of allyl chloride and about 0.05 to less than two moles of a liquid aromatic hydrocarbon solvent per mole of the dialkyl ether, at a temperature within a range of about 5° C. to 200° C., it being especially noted that the process is directed to toluene, xylene, and benzene as the hydrocarbon solvents.

THE INVENTION

The present invention deals with a method for preparing phenyl-containing organosilicon intermediates using an aromatic halogenated solvent during the coupling reaction involving a phenyl Grignard reagent and a precursor halosilane. The process comprises contacting a phenyl halide with magnesium in a solvent such as ether, or aromatic halogenated/ether mixtures to form a Grignard reagent, and contacting the Grignard reagent with a precursor chlorosilane in an aromatic halogenated solvent to form the desired organosilicon intermediates, and then filtering and distilling to acquire the organosilicon intermediate reaction product.

More specifically, the invention deals with a method for preparing phenyl-containing organosilicon intermediates, wherein the method comprises contacting a phenyl-containing Grignard reagent with a precursor chlorosilane having the general formula $R_aSiX_{4-a}$ wherein each R is independently selected from the phenyl group, the vinyl group, the methyl group, or hydrogen, X is chlorine or bromine and $a$ has a value of 0, 1, or 2, and allowing the Grignard reagent to react with the precursor chlorosilane to form a phenyl-containing organosilicon intermediate, wherein the reaction is carried out in the presence of a solvent comprising the group: a mixture of a dialkyl ether solvent and aromatic halogenated solvent or a mixture of a mixture of dialkyl ether solvents and an aromatic halogenated solvent.

In a further embodiment, there is a method for preparing phenyl-containing organosilicon intermediates wherein the method comprises contacting magnesium metal with a mixture comprising a phenylhalide wherein the halide is selected from chlorine and bromine; a precursor chlorosilane having the general formula $R_aSiX_{4-a}$ wherein each R is independently selected from the phenyl group, the vinyl group, the methyl group, or hydrogen, X is chlorine or bromine, and $a$ has a value of 0, 1, or 2; a co-solvent selected from the group consisting of a mixture of a dialkyl ether solvent and an aromatic halogenated solvent or a mixture of a mixture of dialkyl ether solvents and an aromatic halogenated solvent.

Although the phenyl Grignard reagent can be prepared separately, and then used in the coupling reaction with the mixture of a dialkyl ether and aromatic halogenated solvent,

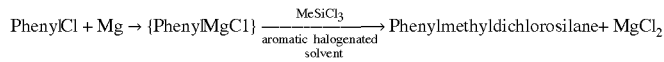

or a mixture of a mixture of dialkyl ethers and aromatic halogenated solvent, it is preferred that all of these embodiments are "one-step" processes for the preparation of phenyl-containing organosilicon intermediates because it is not necessary to isolate an intermediate Grignard-type reagent in the process and then further react this Grignard-type reagent with the precursor halosilane to form the organosilicon intermediates. Further, it is not necessary to conduct a separate solubilization step on the resulting product slurry to facilitate recovery of the organosilicon intermediates and the excess solvents.

The magnesium metal used in this invention can be any of the known forms of the metal that are currently used for Grignard-type reactions. For example, the metal can be any of those known in the art that are in the form of powder, flakes, granules, chips, lumps, and shavings, and the like.

Contact of the magnesium metal with the phenyl halide can be undertaken in standard type reactors suitable for running Grignard type reactions. The reactor can be a batch, semi-batch, or continuous type of reactor. A preferred reactor is a continuous reactor. The environment in which the present method is carried out should be inert for best results. Therefore, in a preferred method, the reactor is purged and blanketed with an inert gas such as, for example, nitrogen or argon.

Generally, the initial charge of magnesium metal is placed in the reactor containing a co-solvent mixture. The phenyl halide in additional co-solvent is then fed to the reactor at a controlled rate. Once the reaction is started, the mole ratio of magnesium to the phenyl halide fed to the reactor is not critical and can be varied within wide limits. In a batch process, it is preferred that the final mole ratios of magnesium to phenyl halide provide the phenyl halide in sufficient excess to ensure essentially total conversion of the magnesium to the magnesium salts. When the present process is conducted as a continuous process, the magnesium metal is typically present in excess in relation to the phenyl halide fed to the reactor. In such a case, the rate of feed of the phenyl halide to the reactor can be controlled to ensure acceptable levels of conversion of the phenyl halide to the organosilicon intermediates and, minimal presence of the unreacted phenyl magnesium halide complexes. Any excess phenyl halide and/or solvents can be captured and recycled to the reactor.

Phenyl halides useful in this invention are those described by the formula RX, wherein R is phenyl and X is selected from chlorine or bromine atoms. Preferred for this invention is phenyl chloride.

Chlorosilanes useful as precursor silanes in this invention have the general formula $R_aSiX_{4-a}$ wherein each R is independently selected from the phenyl group, the vinyl group, the methyl group, or hydrogen, X is chlorine or bromine and $a$ has a value of 0, 1, or 2.

Such silanes include, for example, silicon tetrachloride, methyltrichlorosilane, dimethyldichlorosilane, phenylmethyldichlorosilane, phenyltrichlorosilane, diphenyldichlorosilane, vinyltrichlorosilane, hydridotrichlorosilane, divinyldichlorosilane, methylvinyldichlorosilane, phenylvinyldichlorosilane, hydridomethyldichlorosilane, hydridophenyldichlorosilane, hydridovinyldichlorosilane and dihydridodichlorosilane, and the like.

The dialkyl ethers useful in this invention include, for example, dimethyl ether, diethyl ether, ethylmethyl ether, n-butylmethyl ether, n-butylethyl ether, di-n-butyl ether, di-isobutyl ether, isobutylmethyl ether, and isobutylethyl ether, and the like. The preferred ether is diethyl ether.

For the formation of the Grignard reagent, the solvent can be selected from ether, an aromatic halogenated solvent, a mixture of a mixture of ether/aromatic halogenated co-solvent, or a mixture of a mixture of ethers and an aromatic halogenated solvent, and the like, it being preferred to use the mixture of an ether/aromatic halogenated solvent so that the coupling reaction can be carried out in the presence of the aromatic halogenated solvent, according to this invention, without having to change solvents or remove additional solvents. For the coupling reaction, it is preferred to use a mixture of dialkyl ether and an aromatic halogenated solvent.

Further, for the coupling reaction between the Grignard reagent and the precursor organohalosilane, it is preferred that the amount of ether in the co-solvent mixture be as small as is possible and therefore, it is preferred that the ratio of ether to the aromatic halogenated solvent be in the range of about 0.2:2 to 0.5:2.

The inventors herein have discovered that this method provides very low viscosity slurries from which the $MgCl_2$ can be separated easily and essentially completely and it leads to substantial improvements in mass transfer and allows for a significant reduction in the total amount of solvent required for the reaction when compared to prior art methods. Generally, this method does not require an initiator for the reaction.

EXAMPLES

Example 1

The apparatus for the following examples consisted of a 3-necked, 500 ml, round bottomed glass flask resting on a heating mantle and a supporting jack, the glass flask being adapted with a mechanical stirrer in the central neck, a Claisen adapter with an addition funnel, a rubber septum for sampling, a second Claisen adapter in the third neck of the flask, that holds a thermometer and a ten bulb water condenser, surmounted by a dry ice/isopropanol reflux condenser with a dry ice condenser surmounted on the top of the isopropanol condenser. The apparatus is also equipped with a nitrogen inlet system.

A Grignard reagent, phenylmagnesiumchloride in diethyl ether was prepared by the reaction of chlorobenzene with magnesium metal at about 170° C. under pressure in a high pressure Grignard reactor.

In the preparation of the phenyl-containing chlorosilane, methyltrichlorosilane as the precursor organohalosilane (230.3 grams, 1.54 moles) and chlorobenzene (253 grams, 2.24 moles) were loaded into a 1 liter glass flask equipped essentially as the apparatus described above, and heated slowly to 40° C. Liquid Grignard reagent from above, in diethyl ether (250 ml.), was loaded into an addition funnel and slowly added to the silane solution. The reaction exothermed gently to 47° C. The addition was completed in approximately 2.5 hours. A very flowable reaction mixture was obtained. Upon standing at room temperature $MgCl_2$ readily precipitated. No second layer of $MgCl_2$ was observed after several days standing. Gas Chromatography (GC) analysis of the reaction mixture showed that 12 GC area % of $PhMeSiCl_2$, 1 GC area % of $Ph_2SiMeCl$, 43 GC area % of PhCl, 21GC area % of unreacted $MeSiCl_3$, 18 GC area % of diethyl ether, was detected by the analysis. There was no indication of the presence of biphenyl.

Example 2

Using PhMgCl in PhCl Grignard wherein the Ratio is 1:0.08:4 PhMgCl/Diethyl Ether/PhCl/Coupling Mole Ratio 1:4:3 PhMgCl/PhCl/MeSiCl₃

A coupling reaction of PhMgCl/MeSiCl₃ to form PhMeSiCl₂ was performed in the presence of chlorobenzene in a mole ratio of 1:4:3 of PhMgCl/PhCl/MeSiCl₃ PhMgCl in chlorobenzene (250 Milliliters, 0.424 mole) was transferred to a 500 milliliter addition funnel via nitrogen pressure and transfer tubes. This equates to 0.424 mole of PhMgCl, and 1.70 mole of PhCl. MeSiCl₃ (191.12 grams, 1.279 moles) was transferred into a 1000 milliliter round bottom flask. The addition funnel with the PhMgCl Grignard agent was then attached and nitrogen was supplied to provide an inert atmosphere in the system. The addition of the Grignard solution took place over a 27 minute period. The solution appeared a milky green color and remained very flowable throughout the experiment. The maximum exothermic temperature reached was 78° C. The reaction mixture was allowed to cool. After all of the solids settled, the final appearance was a yellow liquid on top of a greenish-white, very silty, solid. Gas Chromatography analysis with dual internal standards of heptane and tridecane was performed on the liquid portion of the mixture and it showed 5 weight % PhMeSiCl₂, 15 weight % MeSiCl₃, 3.5 weight % Ph₂MeSiCl and the remainder was mostly PhCl, diethyl ether, benzene and other minor impurities.

Coupling mole ratio of 1:4:2 PhMgCl:PhCl:MeSiCl₃

PhMgCl in chlorobenzene (250 milliliters, 0.424 mole) was transferred to a 500 milliliter addition funnel via nitrogen pressure and transfer tubes. This equates to 0.424 mole PhMgCl, and 1.70 mole of PhCl. MeSiCl₃ (125.9 grams, 0.84 mole) was transferred into a 1000 milliliter round bottomed flask. The addition funnel with the PhMgCl Grignard was then attached and nitrogen was supplied to provide an inert atmosphere in the system. Addition of the Grignard solution took place over a period of 37 minutes. The solution appeared a milky green color and remained very flowable throughout the experiment. The maximum exothermic temperature reached was 80° C. The reaction mixture was allowed to cool. After all of the solids settled the final appearance was a yellow liquid on top of a greenish-white, very silty, solid. Gas Chromatography analysis with dual internal standards of heptane and tridecane was performed on the liquid portion of the mixture and it showed 5 weight % PhMeSiCl₂, 15 weight % MeSiCl₃, 6 weight % Ph₂MeSiCl and the remainder was mostly PhCl, diethyl ether, benzene and other minor impurities.

Example 4

Using PhMgCl in Diethyl Ether with a Mole Ratio of PhMgCl:Diethyl Ether is 1:4/Coupling Mole Ratio of 1:4: 3:3 for PhMgCl:Diethyl Ether:PhCl:MeSiCl₃

A coupling reaction of PhMgCl/MeSiCl₃ to yield PhMeSiCl₂ was performed in the presence of diethyl ether and chlorobenzene in a mole ratio of 1:4:3:3 of PhMgCl/diethyl ether/PhCl/MeSiCl₃. The mole ratio of the PhMgCl Grignard solution in diethyl ether was 1:4 PhMgCl/diethyl ether.

Approximately 250 milliliters of this solution was transferred to a 500 milliliter addition funnel via nitrogen pressure and transfer tubes. This equates to about 0.5 mol of PhMgCl and 2.0 mole of diethyl ether. MeSiCl₃ (224.2 grams, 1.5 mol) and chlorobenzene (112.63 grams, 1.0 mol) were added to a 1000 milliliter round bottomed flask. Addition of the Grignard solution took place over a time period of 32 minutes. The solution turned a very, very dark orange brown color and remained flowable throughout the experiment. The maximum exothermic temperature reached was 65.5° C. When agitation was stopped, solids settling began almost immediately. The reaction mixture was allowed to cool. G.C. analysis with dual internal standards as in the previous examples was performed on the liquid portion of the mixture which resulted in 16 weight % PhMeSiCl₂, 15 weight % MeSiCl₃, 0.6 weight % Ph₂MeSiCl and the remainder was mostly PhCl, diethyl ether, benzene and other minor impurities.

Coupling Mole Ratio of 1:4:2:5 for PhMgCl/Diethyl Ether/PhCl/MeSiCl₃

A coupling reaction of PhMgCl/MeSiCl₃ to yield PhMeSiCl₂ was performed in the presence of diethyl ether and chlorobenzene in a mole ratio of 1:4:2:5 of PhMgCl/diethyl ether/PhCl/MeSiCl₃, The mole ratio of the PhMgCl Grignard solution in diethyl ether was 1:4 PhMgCl/diethyl ether. Approximately 250 milliliters of this solution was transferred to a 500 milliliter addition funnel via nitrogen pressure and transfer tubes. This equates to about 0.5 mol of PhMgCl and 2.0 mol of diethyl ether. MeSiCl₃ (373.7 grams, 2.5 mol) and chlorobenzene (112.63 grams, 1.0 mol) were added to a 1000 milliliter round bottomed flask. Addition of the Grignard solution took place over a time of 32 minutes. The solution turned a very, very dark orange brown color and remained flowable throughout the experiment. The maximum exothermic temperature reached was 65° C. When agitation was stopped, solids began settling almost immediately. The reaction mixture was allowed to cool. G.C. analysis with dual internal standards as in the previous examples was performed on the liquid portion of the mixture resulted in 13.4 weight % PhMeSiCl₂, 25 weight % MeSiCl₃, 0.4 weight % of Ph₂MeSiCl and the remainder was mostly PhCl, diethyl ether, benzene and other minor impurities.

Example 5

Using PhMgCl in PhCl with a Mole Ratio of PhMgCl/PhCl of 1:4/Coupling with MeViSiCl₂ Using PhMgCl in PhCl with a Mole Ratio of PhMgCl/PhCl/MeViSiCl₂ of 1:5.5:1.5

PhMgCl in PhCl (640 milliliters, 1 mol) was quickly added to MeViSiCl₂ (1.54 moles, 218 grams) in PhCl (1.48 moles, 166.22 grams) in the reactor at an average rate of 25 milliliters per minutes. The reaction was exothermic, increasing in temperature as the PhMgCl/PhCl was added from 25 to a maximum of 67° C. The mixture remained flowable throughout the coupling reaction. Once the total of the PhMgCl had been transferred, the temperature started decreasing until it returned to ambient temperature. The mixture was allowed to settle overnight and it clearly divided into a clear reddish liquid phase and a white solid precipitate. G.C. analysis of the reaction mixture resulted in an 11 weight % PhMeViSiCl, 4 weight % of MeViSiCl₂, 75 weight percent of chlorobenzene and other minor impurities.

Coupling Reaction of MeSiCl3 in PhCl with PhMgCl in PhCl with a Mole Ratio of PhMgCl/PhCl of 1:4 Wherein the Mole Ration of PhMgCl:PhCl:MeSiCl₃ is 1:5.5:3

PhMgCl in PhCl (640 milliliters, 1 mole) was added to MeSiCl₃ (448.75 grams, 3 moles) in PhCl (1.55 moles, 175.08 grams) in the reactor at an average rate of 19 milliliters per minute. The reaction was exothermic to a maximum of 65° C. The mixture remained very flowable throughout coupling. Once the total of the PhMgCl had been transferred, the temperature started decreasing until it returned to ambient temperature. The mixture was allowed to settle overnight and it clearly divided into a clear reddish liquid phase and a white solid precipitate. GC analysis of the reaction mixture resulted in 8 weight % Ph$_2$MeSiCl$_2$, 4 weight % MeSiCl$_3$, 79 weight % chlorobenzene and other minor impurities.

What is claimed is:

1. A method for preparing phenyl-containing organosilicon intermediates, the method comprising:
   (I) contacting a phenyl-containing Grignard reagent with a precursor chlorosilane having the general formula R$_a$SiX$_{4-a}$ wherein each R is independently selected from the phenyl group, the vinyl group, the methyl group, or hydrogen, X is chlorine or bromine and $_a$ has a value of 0, 1, or 2;
   (II) allowing the phenyl-containing Grignard reagent to react with the precursor chlorosilane to form a phenyl-containing organosilicon intermediate, wherein the reaction is carried out in the presence of a solvent comprising the group:
      (i) a mixture of a dialkyl ether solvent and an aromatic halogenated solvent;
      (ii) a mixture of a mixture of dialkyl ether solvents and an aromatic halogenated solvent.

2. A process as claimed in claim 1 wherein the process is carried out at a temperature of about 0° C. to about 200° C.

3. A process as claimed in claim 1 wherein the process is carried out at a pressure of about ambient pressure to about 200 psig.

4. A process as claimed in claim 1 wherein the process is carried out in an inert atmosphere.

5. A process as claimed in claim 4 wherein the inert atmosphere is nitrogen.

6. A process as claimed in claim 1 wherein the ratio of aromatic halogenated to the dialkyl ether solvent is in the range of about 0.2:2 to 0.5:2.

7. A process as claimed in claim 1 wherein the dialkyl ether is diethyl ether.

8. A method for preparing phenyl-containing organosilicon intermediates, the method comprising contacting magnesium metal with a mixture comprising:
   (i) a phenylhalide wherein the halide is selected from chlorine and bromine;
   (ii) a chlorosilane having the general formula R$_a$SiX$_{4-a}$ wherein each R is independently selected from the phenyl group, the vinyl group, the methyl group, or hydrogen, X is chlorine or bromine, and $_a$ has a value of 0, 1, or 2;
   (iii) a co-solvent selected from the group consisting of
      (a) a mixture of a dialkyl ether solvent and an aromatic halogenated solvent;
      (b) a mixture of a mixture of dialkyl ether solvents and an aromatic halogenated solvent.

9. A process as claimed in claim 8 wherein the process is carried out at a temperature of about 0° C. to about 200° C.

10. A process as claimed in claim 8 wherein the process is carried out at a pressure of about ambient pressure to about 200 psig.

11. A process as claimed in claim 8 wherein the process is carried out in an inert atmosphere.

12. A process as claimed in claim 11 wherein the inert atmosphere is nitrogen.

13. A process as claimed in claim 8 wherein the ratio of the aromatic halogenated to the dialkyl ether solvent is in the range of about 0.2:2 to 0.5:2.

14. A process as claimed in claim 8 wherein the dialkyl ether is diethyl ether.

15. A process as claimed in claim 1 wherein the dialkyl ether is diethyl ether and the co-solvent is chlorobenzene.

16. A process as claimed in claim 8 wherein the dialkyl ether is diethyl ether and the co-solvent is chlorobenzene.

17. A process as claimed in claim 8 wherein the process is a continuous process.

18. A process as claimed in claim 16 wherein the chlorobenzene solvent and the dialkyl ether solvent are cycled back to a Grignard reactor.

19. A process as claimed in claim 8 wherein the precursor chlorosilane is selected from the group consisting of silicon tetrachloride, methyltrichlorosilane, dimethyldichlorosilane, phenylmethyldichlorosilane, phenyltrichlorosilane, diphenyldichlorosilane, vinyltrichlorosilane, hydridotrichlorosilane, divinyldichlorosilane, methylvinyldichlorosilane, phenylvinyldichlorosilane, hydridomethyldichlorosilane, hydridophenyldichlorosilane, hydridovinyldichlorosilane and dihydridodichlorosilane.

* * * * *